US009989476B2

(12) United States Patent
Vähäsalo et al.

(10) Patent No.: US 9,989,476 B2
(45) Date of Patent: Jun. 5, 2018

(54) OPTICAL DETERMINATION OF ANIONIC CHARGE IN A PROCESS STREAM

(71) Applicant: Kemira Oyj, Helsinki (FI)

(72) Inventors: Lari Vähäsalo, Espoo (FI); Iiris Joensuu, Espoo (FI); Marjatta Piironen, Espoo (FI)

(73) Assignee: KEMIRA OYJ, Helsinki (FI)

( * ) Notice: Subject to any disclaimer, the term of this patent is extended or adjusted under 35 U.S.C. 154(b) by 0 days. days.

(21) Appl. No.: 15/038,483

(22) PCT Filed: Nov. 18, 2014

(86) PCT No.: PCT/FI2014/050870
§ 371 (c)(1),
(2) Date: May 23, 2016

(87) PCT Pub. No.: WO2015/075306
PCT Pub. Date: May 28, 2015

(65) Prior Publication Data
US 2016/0305890 A1    Oct. 20, 2016

(30) Foreign Application Priority Data

Nov. 24, 2013  (FI) .................................... 20136173

(51) Int. Cl.
*G01N 21/85*  (2006.01)
*B03B 7/00*  (2006.01)
(Continued)

(52) U.S. Cl.
CPC ............... *G01N 21/85* (2013.01); *B03B 7/00* (2013.01); *C09B 21/00* (2013.01);
(Continued)

(58) Field of Classification Search
CPC .... G01N 21/85; G01N 21/274; G01N 21/314; G01N 21/59; G01N 21/78; G01N 21/82;
(Continued)

(56) References Cited

U.S. PATENT DOCUMENTS 3,819,277 A * 6/1974 Berthelot ............. G01N 21/314
250/233
4,403,861 A * 9/1983 Boisde ...................... G01J 1/36
356/407
(Continued)

FOREIGN PATENT DOCUMENTS

| GB | 638320 A | 6/1950 |
|----|----------|--------|
| WO | WO2008053070 A2 | 5/2008 |
| WO | WO2010031477 A1 | 3/2010 |

OTHER PUBLICATIONS

Fardim P et al: Critical comparison and validation of methods for determination of anionic groups in pulp fibres. Nordic Pulp and Paper Research Journal. vol. 17, No. 3, 2002, pp. 348-351.

*Primary Examiner* — Jennifer Wecker
(74) *Attorney, Agent, or Firm* — Birch, Stewart, Kolasch & Birch, LLP

(57) ABSTRACT

The present invention concerns a method of optical measurement of an aqueous stream, and of processing the results of the measurement in order to determine the anionic charge of the stream, the method being carried out by measuring the light absorption of the stream and predicting the amount of anionic groups in the stream using a mathematical processing, such as mathematical calculations. Particularly, the method includes the steps of adding an amount of a cationic dye to the aqueous stream, measuring the light absorption spectra of the obtained dye-containing stream, and processing the obtained light absorption spectrum using said mathematical processing in order to obtain the anionic charge. The invention also concerns the use of the obtained spec- (Continued)

trum in determining the turbidity of the stream, as well as a device suitable for use in carrying out the method.

19 Claims, 4 Drawing Sheets

(51) Int. Cl.
| | |
|---|---|
| C09B 67/32 | (2006.01) |
| G01N 21/27 | (2006.01) |
| G01N 21/59 | (2006.01) |
| G01N 21/82 | (2006.01) |
| G01N 31/22 | (2006.01) |
| G01N 33/18 | (2006.01) |
| D21H 23/08 | (2006.01) |
| G01N 15/06 | (2006.01) |
| G01N 21/31 | (2006.01) |
| G01N 33/34 | (2006.01) |
| G01N 21/78 | (2006.01) |
| D21H 23/78 | (2006.01) |
| C09B 21/00 | (2006.01) |
| G01N 15/00 | (2006.01) |
| C02F 1/52 | (2006.01) |
| G01N 21/83 | (2006.01) |
| G01N 21/84 | (2006.01) |
| G01N 27/447 | (2006.01) |
| G01N 21/77 | (2006.01) |

(52) U.S. Cl.
CPC ......... *C09B 67/0075* (2013.01); *D21H 23/08* (2013.01); *D21H 23/78* (2013.01); *G01N 15/06* (2013.01); G01N 21/274 (2013.01); G01N 21/314 (2013.01); *G01N 21/59* (2013.01); *G01N 21/78* (2013.01); *G01N 21/82* (2013.01); *G01N 31/22* (2013.01); *G01N 33/182* (2013.01); *G01N 33/343* (2013.01); C02F 1/5209 (2013.01); G01N 21/83 (2013.01); G01N 27/447 (2013.01); G01N 2015/0053 (2013.01); G01N 2015/0092 (2013.01); G01N 2015/0693 (2013.01); G01N 2021/3155 (2013.01); G01N 2021/7783 (2013.01); G01N 2021/8411 (2013.01); G01N 2021/8416 (2013.01); G01N 2021/8557 (2013.01); G01N 2201/127 (2013.01); G01N 2201/129 (2013.01)

(58) Field of Classification Search
CPC ...... G01N 15/06; G01N 31/22; G01N 33/182; G01N 33/343; B03B 7/00; C09B 67/0075; D21H 23/08
See application file for complete search history.

(56) References Cited

U.S. PATENT DOCUMENTS

| | | | | |
|---|---|---|---|---|
| 2002/0010972 | A1* | 1/2002 | Buentello | C09B 67/0073 8/611 |
| 2005/0139337 | A1* | 6/2005 | Li | G01N 21/33 162/49 |
| 2008/0299665 | A1* | 12/2008 | Xiao | G01N 21/78 436/85 |
| 2012/0072000 | A1* | 3/2012 | Saren | D21G 9/0018 700/104 |
| 2013/0220922 | A1* | 8/2013 | Joensuu | B01D 21/01 210/632 |
| 2014/0343872 | A1* | 11/2014 | Ilmola | G01N 33/343 702/25 |

* cited by examiner

OPTICAL DETERMINATION OF ANIONIC CHARGE IN A PROCESS STREAM

BACKGROUND OF THE INVENTION

Field of the Invention

The present invention relates to an optical method for the determination of anionic groups in a stream, and optionally for the determination of the turbidity of the stream. If desired, the stream can be fractionated, according to the particle size or mass of any substances therein, or both size and mass, prior to the determination(s).

Description of Related Art

Charged groups originating from pulp suspensions and other slurries can have a significant effect on the behavior of the slurry in chemical reactions. These charged groups can react with and bind to various additives and particles added to the slurry, as well as cause flocculation. Therefore, determining the content of such charged groups is important in determining the amount of additives to be used, and to determine whether these charged groups need to be separately removed.

Some of the methods traditionally used for measuring the content of anionic groups in a sample have been labor- and time-consuming. Simpler alternatives include titration (conductometric or potentiometric) of laboratory samples of the slurry. However, these methods cannot be performed directly in flowing stream, and they require that the anionic groups are in their protonated form.

An alternative optical method is described in WO2004063724 and F1991963. In WO2004063724 the sample is first washed in order to remove dissolved and small particles from the pulp fibers. Dye is added, the sample is filtrated and the amount of unadsorbed dye is measured. In F1991963, the change in absorbance is measured as a function of added anionic or cationic polymer from which a calibration curve is constructed. This method requires time consuming titration of a separate laboratory sample, and it requires a calibration curve to be constructed for each different type of sample. Thus, these methods both require additional steps such as washing and filtration of the sample, and the measurements in both methods are carried out on laboratory samples, and do not allow direct measurement in a flowing stream.

These methods are based on the measurement of one single wavelength, rendering them sensitive towards interference. Therefore they do not provide a reliable result of the charge. These methods also require a calibration.

Therefore, there exists a need for methods of determining the total charge of streams or their particle populations, which methods should be fast, simple and possible to carry out directly on flowing streams, whereby separate sample collection can be avoided.

SUMMARY OF THE INVENTION

It is an object of the present invention to provide a novel method and device for determining the total anionic charge of streams, such as side-draws of process streams.

Particularly, it is an object of the present invention to provide a method and device for determining the anionic charge, where the measurements can be carried out directly from the stream, without requiring separate sample collectioning.

It is another particular object of the invention to provide a method and device for determining the different anionic charges of different particle fractions or populations of the stream. These different particle fractions should preferably be possible to analyze using one single calibration curve.

These and other objects, together with the advantages thereof over known methods and devices, are achieved by the present invention, as hereinafter described and claimed.

The method is based on light absorption measurement of a cationic dye added to a stream, according to the Beer-Lambert Law, followed by an estimation, e.g. by calculation, of the number of anionic groups in the stream. A measurement of the light transmittance is, however, equally useful. The method can be used for determining the total amount of anionic groups in the substances contained in the stream, such as dissolved polymers, colloidal particles and even dispersed particles. For paper machine samples, the method can also be used for example to determine the cationic demand of a filtrate and the zeta potential of fibers, particularly when used in combination with a stream fractionation system, since such a system separates dissolved and colloidal material from larger particles and said fibers. Particles can be separated into one or more particle populations according to their size and/or mass, e.g. by separating them into colloids, stickies, pitch, fines, fillers and agglomerates.

Additionally, the present method and device allow the calculation of the turbidity of the stream from the same measured absorption spectrum.

Thus, the present invention concerns a method of optical measurement of an aqueous stream, and of processing the results of the measurement in order to determine the anionic charge of the stream, the method being carried out by measuring the light absorption of the stream and predicting the amount of anionic groups in the stream using mathematical processing, such as mathematical calculations.

More specifically, the method of the present invention is characterized by what is stated in the characterizing part of Claim 1.

Further, the use of the present invention for determining the turbidity of the stream is characterized by what is stated in Claim 15, and the device of the present invention is characterized by what is stated in the characterizing part of Claim 17.

Considerable advantages are obtained by means of the invention. Thus, the present invention provides a simple spectrophotometric method for the determination of anionic groups in a stream.

The method is convenient and fast, and does not require any pretreatment except a possible dilution of the sample or the stream before a dye is added and before measurement of the light absorption spectrum. Thus, any aqueous stream can be analyzed. The sample or stream can be a dilute stream only containing dissolved and colloidal substances, or dispersed particles, and it can also contain for example wood fibers. Anything from dissolved molecules to large aggregates can be analyzed.

The measurements can be done directly on a flowing stream, on-line, i.e. without a separate sample collection step and laboratory measurements. However, the method is possible to use on either flowing or stationary samples, inline and online or in a laboratory.

It is possible to determine turbidity from the same absorption spectra as the amount of dye (or amount of anionic groups), and the variations in the turbidity do not cause problems for the estimation of the content of anionic groups.

The invention can also be used to determine whether or not cationic polymers or other chemicals added to process streams perform as expected, and to monitor that chemicals are not overdosed (which overdosing could result in unwanted, often costly, runnability problems, or aggregation).

Only one general calibration model needs to be constructed, according to an embodiment of the invention, instead of new calibrations being needed for each measurement. If the stream is fractionated according to e.g. particle size or mass, new type of information will be obtained of the relation between particle size and anionic charge, for example in the detection of anionic populations.

Next, the invention will be described more closely with reference to the attached drawings and a detailed description.

DETAILED DESCRIPTION OF EMBODIMENTS OF THE INVENTION

Figure 1:
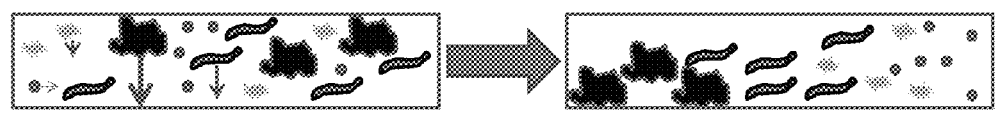
FIG. 1 is a picture illustrating the function of the optional fractionation of the stream to be analyzed according to the invention.

The present invention concerns a method of optical measurement of an aqueous stream, and of processing the results of the measurement in order to determine the anionic charge of the stream.

The method is carried out by measuring the light absorption or light transmittance of the stream and predicting the amount of anionic groups in the stream using mathematical processing, preferably mathematical calculations, in order to obtain results that correlate with the charge of the stream.

According to one option, the mathematical processing or calculations can include, or preferably consist of, derivation, whereby the minimum or maximum value of the derivative at the maximum absorbance area of the dye correlates with the total charge of the stream. The selection of the minimum or maximum value is dependent on the direction of the derivation.

According to another option, the mathematical processing or calculations can include, or preferably consist of, processing the results using a pre-determined calibration model, to which the light absorption values of the obtained spectrum are compared. The result is a value that corresponds to the charge of the stream (generally in SI units).

Thus, the following main steps are carried out in the method:
adding a fixed amount of a cationic dye to the aqueous stream,
measuring the light absorption or transmittance spectra of the obtained dye-containing stream, and
processing the obtained light absorption spectrum using mathematical calculations.

Thereby, by the term "stream" is here meant a flowing or stationary stream, such as an aqueous main stream of a process, a side-draw thereof, or a sample of either of these. In the present invention, it is preferred to obtain a side-draw of the main stream of a process, and carry out the steps of the method on-line on this side-draw, in a flowing state.

The stream is selected, for example from streams containing dissolved or colloidal substances or particles, or both. Particularly, the invention is suitable for use on fibrous streams containing fibrous substances, such as wood fibers. Examples of such streams include pulp, raw water, wire water and circulation water streams of the paper industry, as well as various waste water streams.

The term "colloidal substances" is intended to cover substances formed of particles having a particle size of 2 to 500 nm, and generally existing in dispersed form in the streams analyzed according to the present invention.

The anionic character of the stream is caused by the substances contained therein, which substances contain both cationic and anionic functional groups. Since usually the majority of these charged functional groups are anionic, the substances have an overall anionic charge.

Since the measurements may be conducted directly from the stream, as described above, without separate sample collection and further sample pre-treatments, it may be advantageous to dilute the stream before adding the cationic dye. The stream is preferably diluted when its content of undissolved particles is higher than 5 g/L.

The cationic dye is preferably selected from water-soluble heterocyclic aromatic cationic compounds absorbing light at least at a wavelength of 450-700 nm, more preferably from methylene green and methylene blue, which exhibit the desired absorption in said wavelength region.

The amount of cationic dye added to the stream is typically adjusted to render the desired section of the stream cationic. The amount required for this purpose can also be called the "cationic demand". When added to the stream, the cationic dye will almost immediately adsorb to the anionic groups of any substances in the stream, such as carboxyl groups, whereby also the visible color of the dye will disappear. This is caused by the reduced ability of the reacted (adsorbed) dye to absorb light. Thereby, the stream can be provided with a lasting color only by adding an excess of dye (compared to the amount of anionic groups in the stream).

Thus, a sufficient amount of dye to render the entire dye-treated section of the stream cationic is typically >1 eq (compared to the estimated amount of anionic groups in the stream). This excess of dye can be detected, visually, due to the color of the stream.

Said sufficient amount of dye is preferably estimated based on earlier charge measurements of the same or similar streams, the amount most suitably being 60-120 μmol/l.

In order to ensure that all the anionic groups of the stream have reacted, the dye is allowed to react in the stream. The time required can be short, such as one second or a few seconds (e.g. 3 to 10 seconds), but preferably a time of at least 1 minute is used, more preferably 3 to 10 minutes. Subsequently, the light absorption is measured.

The light absorption measurement of the invention, carried out after the addition and adsorption of the dye, provides the results as a light absorption spectrum, where a baseline indicates the turbidity of the stream to be analyzed, and where the height of the absorption peak(s) correspond to the amount of unreacted (i.e. unadsorbed) cationic dye, or alternatively the reacted (i.e. adsorbed) dye. Generally, the spectrum is obtained at two or more wave lengths, preferably at several equally distributed wavelengths, such as 10 to 20 wavelengths, e.g. 1 to 2 nm apart.

Due to the addition of the dye in excess, and due to the binding of the anionic groups in the stream to the dye, a strong absorption indicates a large amount of free dye in the stream. This further indicates a small amount of anionic groups in the stream.

The spectrum is preferably a UV-Vis spectrum (Ultra Violet-Visual spectrum). Particularly, the absorption results within the wavelength range from 450 nm to 700 nm are included in the spectrum, preferably from 400 to 800 nm, and more preferably for the entire range of 250 nm to 900 nm.

Thus, the method is based on the fact that when a cationic dye is added to a stream or a sample containing anionic groups, the light absorbance spectrum of the stream or the sample is a function of the amount of free light absorbing dye, the amount of anionic groups and the turbidity of the stream or sample.

The thus obtained light absorption spectrum can subsequently be processed using one or more mathematical processing steps. According to one embodiment, this processing is based on the results of a calibration. For calibration purposes, calibration samples are collected, although this can be done well before the measurement of the absorbance spectrum to be processed. These calibration samples, which should have high variation in multiple variables, including at least their turbidity and anionic charge, can contain water, cationic dye, dissolved or colloidal substances, or particles, or a mixture of any of these. The turbidity of the samples corresponds particularly to the content of undissolved particles therein.

Absorbance spectra are then measured from these calibration samples, and the effect of background absorption (or baseline) caused by the turbidity of the samples is neutralized, preferably by comparing it to a reference value, which can be obtained for example from a water sample. However, obtaining a reference value is not necessary when the mathematical processing includes a derivation. This derivation removes the effect of the background, i.e. the turbidity, from the results.

Further mathematical processing steps can be selected from, e.g. smoothing (such as by using data filters or by averaging) and derivation, preferably at least one step of derivation, most suitably by calculating the first derivative of an obtained absorption spectrum. Said and said further mathematical processing steps (and optionally the neutralization of the effect of background absorption) form the used "calibration model".

The mathematical processing model, e.g. utilizing derivation, will give a result that is a measure which is relative to the number of anionic groups in the sample.

According to an alternative embodiment of the invention, the mathematical processing model is, in turn, constructed from the results obtained from a series of calibration samples, with contents that should span the expected variation in the amount of anionic groups and turbidity of the unknown samples.

The calibration model is preferably pre-determined, and can be obtained, for example, by polyelectrolyte titration methods, such as the streaming potential method, or by electrophoretic mobility measurements of the calibration samples, which methods give the anionic charge of these calibration samples.

The results of the calibration will depend also on the used dye, as for example methylene green will give a sufficiently specific absorption spectrum in the wavelength region from 250 nm to 900 nm, although the required results can be obtained also using a more narrow region from 450 nm to 800 nm.

Through multivariate calibration, the measured absorbance spectra of the calibration samples can be used to calculate both the amount of anionic groups and the turbidity of these samples. The multivariate calibration method can for example be the partial least squares (PLS) method or a more complex multivariable calibration method.

Partial least squares (PLS) is a statistical method that can be used to project predicted results (e.g. calibration results) and observable results (e.g. results to be analyzed, obtained from an absorption spectrum), using two different variables, into a linear graph indicating the relation between these variables. Multivariable methods naturally utilize further different variables.

According to a preferred embodiment of the invention, the stream is fractioned, based on the particle size or mass of any substances contained therein, before carrying out the light absorption measurements. The light absorption spectrum is then measured for each of the obtained fractions separately. In this manner, the anionic character can be determined for different fractions separately, these fractions containing different types of particles, generally with different charge characteristics.

The fractioning, or the separation of the particles in the stream into particle populations depending on their mass or charge, or both, can be carried out using the method described in PCT/FI2013/050572, i.e. by conducting the sample to a disintegration channel that is designed so that a liquid flow disintegrates potential flocks in the sample and gradually carries particles of the sample further with the liquid flow.

Alternatively, the fractioning or separation can be carried out by filtering, centrifuging or sedimentation or any other suitable fractioning method. The particle populations thus obtained preferably include two or more of the following: colloids, fibers, and agglomerates, which all may have different charges.

All the steps of the method are preferably carried out in-line. Since the measurements can be carried out directly from the stream, without a separate collection of samples, the method can be used in a continuous or semi-continuous manner, whereby the continuous manner reflects the measurement of the light absorption spectrum directly from the flowing stream, whereas the semi-continuous manner mainly reflects the characteristics of the measurement of the spectra (i.e. frequent repetition of the measurements, but not an essentially constant measurement).

In addition to processing the light absorption spectrum in order to determine the anionic charge of the stream, the same results can be used to determine the turbidity of the same aqueous stream. Particularly, the turbidity is determined by analyzing the background absorption of the light absorption spectrum.

The present invention also concerns a device for the optical measurement of the anionic charge of an aqueous stream in a vessel holding the stream 1. Such a device comprises at least the following units:

2 a dye supply unit in connection with the vessel 1,
3 means for measuring the light absorption or transmittance spectra of the stream,
4 means for processing the obtained light absorption results, and Optionally, according to a specific embodiment of the invention, the device can also include means for obtaining a calibration model 5.

The device is suitable for use in carrying out the above described method of the present invention.

A characterizing feature of the device is that the means for measuring the light absorption 3 is adapted to measure the anionic charge directly from the flow in the vessel for holding the stream 1, without the presence of an intermediate sample holding unit and without the need to transport any samples to separate laboratory facilities or even to separate equipment entities.

The means for processing 4 can be selected, for example from mathematical processing steps of smoothing, averaging and derivation.

The means for obtaining a calibration model 5, in turn, can be selected, for example from means for streaming potential titration or for electrophoretic mobility measurements. Preferably, the means for obtaining the calibration model 5, is selected from means for obtaining a multivariate calibration model, more preferably from means for obtaining a PLS model or a calibration model.

In addition to these units, the device may comprise a stream fractioning unit 6, for separating the stream into fractions according to the particle size or mass of any substances contained therein. Using this fractioning unit 6, the anionic character can be determined separately for different fractions of the stream to be analyzed, the fractions generally containing different types of particles having different charge characteristics.

The streams to be analyzed according to the present invention often contain relatively large particles, for example fibers or pigments, and the method and the device of the present invention can be used to provide the necessary information to be able to, for example estimate the amount of cationic polymers that can be added to a stream in order to, e.g., selectively flocculate dissolved and colloidal particles therein.

The method and the device of the invention can also be used to determine whether or not such cationic polymers or other chemicals perform as expected, and to monitor that chemicals are not overdosed (which overdosing could result in unwanted, often costly, runnability problems, or aggregation).

Thus, the method and device can be used in monitoring and/or controlling and/or optimization of chemical performance and process performance.

The technological areas, where this method can be found particularly useful, include the paper industry including pulp, paper and board manufacturing, water purification technology, environmental analysis, the biofuel industry, and even the medical industry.

The following non-limiting examples are intended merely to illustrate the advantages obtained with the embodiments of the present invention.

EXAMPLES

In the below examples, a so-called fractionation system is used. This is a fractionator described in patent application number PCT/FI2013/050572, and it fractionates dispersions, suspensions and slurries based on the particle size of the particles contained in them.

Example 1—Fractionation and Turbidity Measurement of Wire Water

Figure 2:
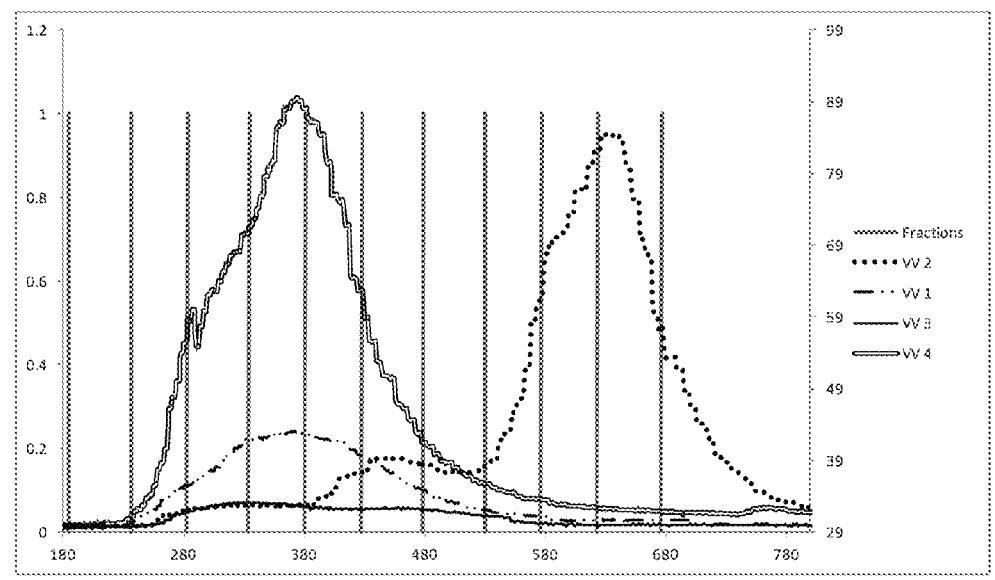
FIG. 2 is a graph showing the turbidity profiles of fractions collected from wire water using continuous fractionation method as described in PCT/FI2013/050572, each fraction containing particles of different sizes compared to the other fractions, with the vertical lines indicating the ten collected fractions, and the X-axis indicating the volume in mL.

Four different wire water samples from different paper manufacturing processes were collected and labeled wire water 1, 2, 3 and 4. Each sample (10 mL) was fractionated by the fractionator system where particles are fractionated according to their mass (see FIG. 1), and the turbidity curves were recorded (see FIG. 2). Larger particles exit the fractionator later than small particles, and are therefore shown on the right of the graph of FIG. 2.

The turbidity of each fraction was calculated by taking the average of the recorded turbidity from the detector (here an inline detector measuring the turbidity directly from the stream flowing through the fractionator) during each 50 mL fraction.

An alternative method is to measure the turbidity using a detector placed in the wire water stream, separately from the fractionator.

Example 2—Absorption Analysis of Dye-Containing Wire Water

The fractions obtained in Example 1 were used here without further modifications.

The above fractionation also resulted in a dilution of the samples, due to the required elution. Thus, from the dilute fractionated stream, ten 50 mL fractions were collected starting at 330 s from the start of the fractionation.

Figure 3:
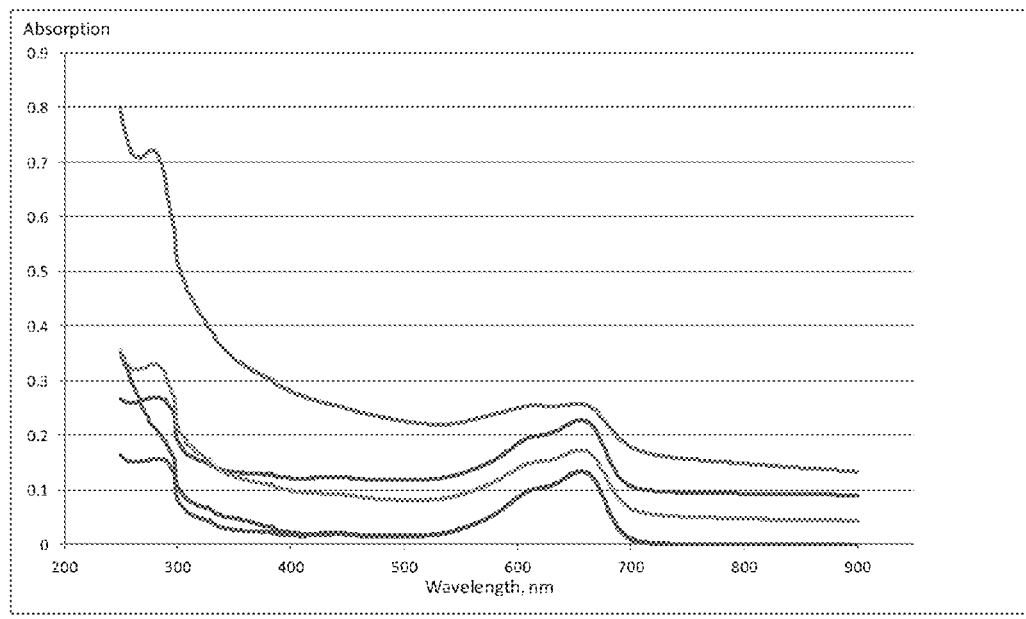
FIG. 3 is a graph showing five light absorption spectra for five wire water samples with different amounts of anionic groups and different turbidities.

For analysis, 3 mL of each sample was placed in a quartz cuvette and 40 µL of 100 µg/mL methylene green was added. The UV-Vis spectrum between 900-250 nm was measured with 2 nm slit and scan speed of 960 nm/min. The light absorption spectra of five samples are shown in FIG. 3 Methylene green absorbs light in the region between 550-700 nm. The stronger the absorption is, the more there is unreacted methylene green in the sample, and thus the anionic charge of the sample is lower.

Figure 4:
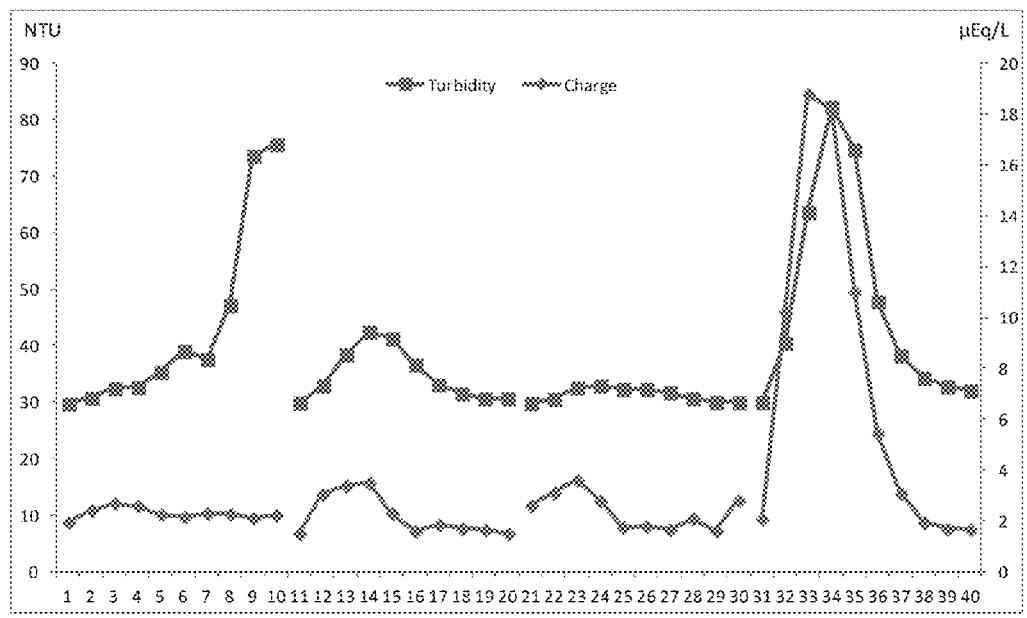
FIG. 4 is a graph showing the turbidity (left axis) and cationic demand (right axis) of wire water fractions, measured by titration.

For comparison, 10 mL of each collected dilute fraction was analyzed for cationic demand using a Mütek streaming potential titrator system, and titrated with 0.0005N cationic polybrene. Each fraction was analyzed three times to obtain reliable results. The results are shown in FIG. 4, where samples 1-10 are fractions of wire water 1, samples 11-20 are fractions of wire water 2, samples 21-30 are fractions of wire water 3 and samples 31-40 are fractions of wire water 4.

The resulting correlation between the measured cationic demand (measured by Mütek) and the calculated anionic charge with the described method was higher than 95%.

From the analyses it became clear that the method according to the invention can be used to measure the anionic charge of a stream reliably and much faster (60 samples in 1 hour) than previously known methods (60 samples in 20 hours for Mütek).

Example 3—Calibration by PLS

For the Partial Least Square (PLS) calibration, a SIMCA-P software was used. The optimal calibration model was achieved with only two components (latent variables, here the turbidity and the absorbance). The Q2 for the modeling was 0.90, in other words the model had extremely good predictability.

Figure 5:
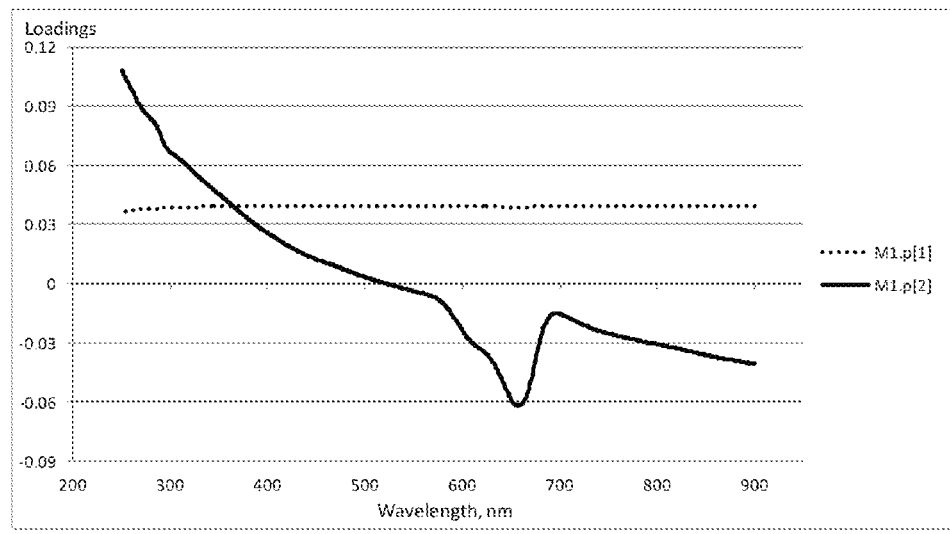
FIG. 5 is a graph showing the loadings of two components in a model for predicting the amount of anionic groups in a sample, component M1 giving an almost straight line, indicating the turbidity baseline, and component M2 giving the absorption.

FIG. 5 shows the loadings for the two components (the latent variables) of the model for predicting the amount of anionic groups in the samples. It is clear from the FIG. that the first component captures the effect of the baseline shift, in other words the turbidity of the sample, whereas the second component gives a strong negative response at wavelengths where methylene green is indicative of a high amount of anionic groups in the sample.

Figure 6:
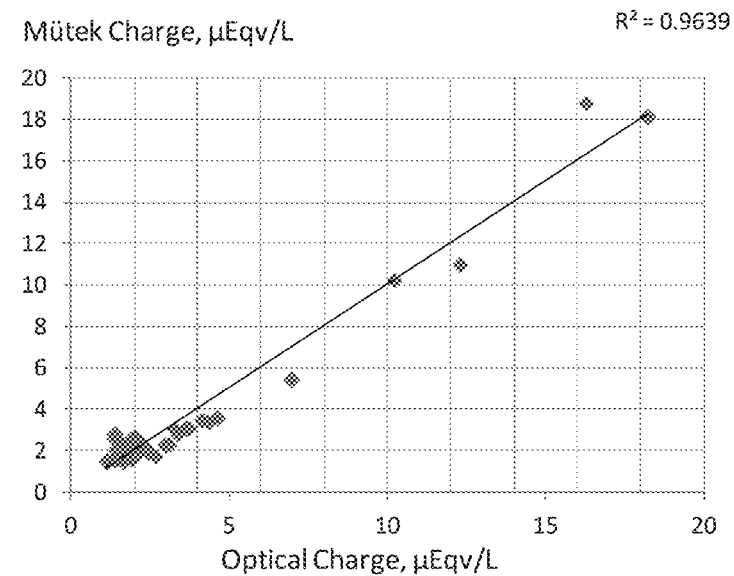
FIG. 6 is a graph showing the predicted and measured anionic groups in wire water samples.

The calibration results are obtained by obtaining the graph of FIG. 5 for several known samples (e.g. water and dye solution). FIG. 6 shows the predicted and measured anionic groups, with a correlation of 98%.

Example 4—Calibration by Derivation

Figure 7:
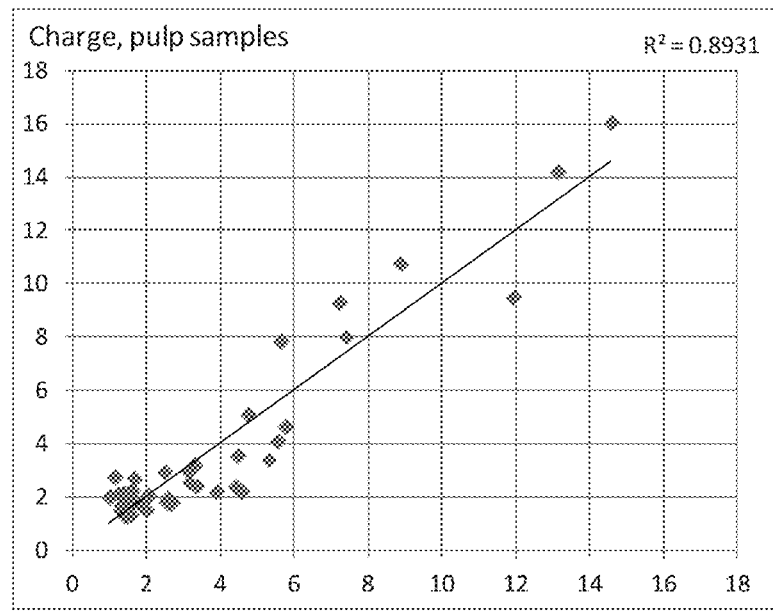
FIG. 7 is a graph showing the predicted and measured anionic groups in pulp samples, using the first derivative of the absorption curve.

Five different samples were collected, ranging from coated broke to fully bleached pine and birch cellulose pulp. Absorption measurements were carried out as described in Example 3. The samples containing fibers had a tendency for sedimentation during the absorption measurements, and this caused the turbidity of the samples to change during the absorption scan, resulting in a lower predictability (88% correlation). This effect was, however, neutralized by taking the first derivative of the absorption curve, giving an improved correlation (95%). The results are shown in FIG. 7.

Example 5—Inline Measurement

After the initial experiments using a bench top laboratory spectrometer, a fiber optic spectrometer was connected to the fractioning system. A constant flow of methylene green solution was added to the sample flow before entering the measurement flow cell. The measurements were conducted as described in the previous examples.

Figure 8:
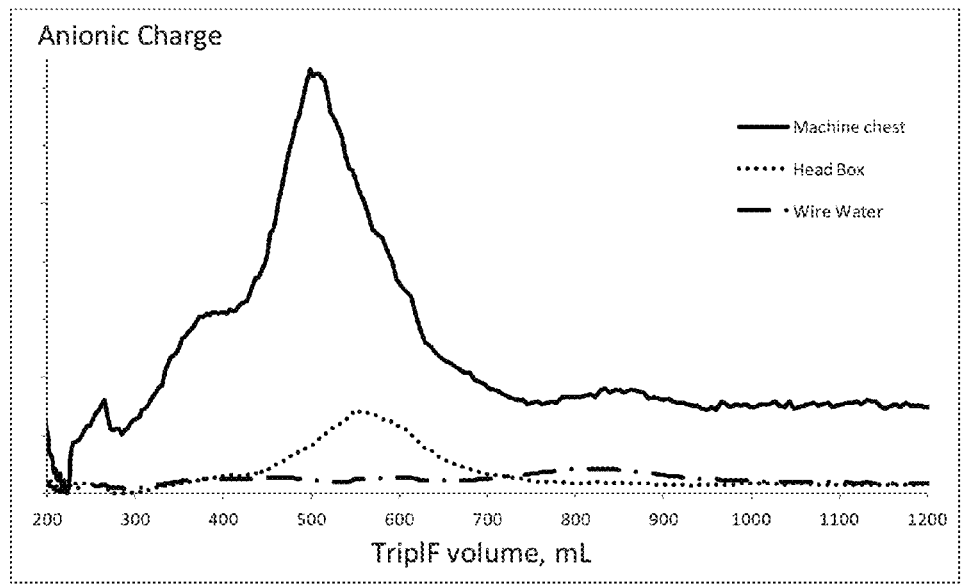
FIG. 8 is a graph showing the anionic charge profile of three paper process samples obtained using an inline method.

Several different samples were analyzed, including wire waters and fiber samples (from the machine chest and the head box). In FIG. 8, the anionic charge profile of the mentioned three exemplary paper process samples is shown.

These results clearly indicate that the fiber optic spectrometer connected to the system is highly suitable for use in inline analyses according to the present invention.

From these results, it can also be seen that the total anionic charge is much lower for the headbox sample compared to the machine chest sample. The reason is the addition of cationic wet end starch and retention aid to the latter. The peak anionic charge occurs in the fraction containing fibers. In the wire water sample, the anionic charge is concentrated to the largest particles, which are not present in the headbox sample. This indicates that the aggregates formed in the wire water still possess some anionic charge.

The invention claimed is:

1. A method of optical measurement of an aqueous stream, and of processing the results of the measurement in order to determine the anionic charge of the stream, the method being carried out by measuring the light absorption or transmittance of the stream and predicting the total amount of anionic groups in the stream, further comprising:
    adding a fixed amount of a cationic dye to the aqueous stream,
    measuring the light absorption or transmittance spectra of the obtained dye-containing stream, and
    obtaining the anionic charge of said aqueous stream by processing the obtained light absorption spectrum using mathematical processing steps of derivation, whereby the minimum or maximum value of the derivative at the maximum absorbance area of the dye is applied in the calculations so that it correlates with the total charge of the stream,
wherein said aqueous stream comprises at least dissolved and colloidal substances.

2. The method according to claim 1, comprising selecting the aqueous stream from at least one of fibrous streams, pulp, raw water, wire water, circulation water streams of paper industry, and waste water streams.

3. The method according to claim 1, further comprising obtaining a side-draw of a main process stream.

4. The method according to claim 1, further comprising diluting the stream before adding the cationic dye.

5. The method according to claim 1, further comprising selecting the cationic dye from water-soluble heterocyclic aromatic cationic compounds absorbing light at a wavelength of 400 nm-700 nm.

6. The method according to claim 1, further comprising adding a sufficient amount of the cationic dye to the stream to render the desired section of the stream cationic.

7. The method according to claim 1, further comprising allowing the cationic dye to react in the stream for at least 1 second before measuring the light absorption.

8. The method according to claim 1, further comprising fractioning the stream according to the particle size or mass, or both, of the substances contained therein, before carrying out the light absorption measurements on one or more of the obtained fractions.

9. The method according to claim 1, further comprising measuring the light absorption spectra of the stream for the wavelength range from 450 nm to 800 nm.

10. The method according to claim 1, further comprising determining a calibration model by measuring the anionic charge of a number of calibration samples.

11. The method according to claim 1, further comprising determining the calibration model by measuring the charge of a number of different calibration samples with variable turbidity and anionic charge, measuring the absorbance corresponding to the obtained charges and neutralizing the effect of background absorption caused by turbidity in the samples by comparing it to a reference value.

12. The method according to claim 10, further comprising the calibration model being a multivariate calibration model.

13. The method according to claim 1, further comprising all the steps of the method being carried out online or in-line.

14. The method according to claim 1, further comprising the step of using the light absorption results to determine the turbidity of an aqueous stream.

15. The method according to claim 1, wherein the turbidity is determined by analyzing the background absorption of the light absorption spectrum.

16. A device for the optical measurement of the anionic charge of an aqueous stream in a vessel holding the stream, comprising:
    a dye supply unit, in connection with the vessel,
    means for measuring the light absorption or transmittance spectra of the stream, and
    means for processing the obtained light absorption or transmittance results, wherein the means for processing have been selected from mathematical processing steps of derivation, whereby the means for processing is adapted to apply the minimum or maximum value of the derivative at the maximum absorbance area of the dye in the calculations so that it correlates with the total charge of the stream, wherein the means for measuring the light absorption is adapted to measure the anionic charge of said aqueous stream directly from the flow in the vessel for holding the stream, wherein said aqueous stream comprises at least one of dissolved and colloidal substances, wherein the device further comprises a stream fractioning unit for separating the stream into fractions according to the particle size of any substances contained therein.

17. The device according to claim 16, wherein the means for processing include means for obtaining a calibration model.

18. The device according to claim 17, wherein the means for obtaining a calibration model have been selected from means for streaming potential titration or for electrophoretic mobility measurements.

19. The device according to claim 17, wherein the means for obtaining the calibration model have been selected from means for obtaining a multivariate calibration model.

\* \* \* \* \*